US007967768B2

(12) United States Patent
Watts (10) Patent No.: US 7,967,768 B2
(45) Date of Patent: Jun. 28, 2011

(54) ANKLE-FOOT ORTHOSIS (76) Inventor: Robert J. Watts, Hampshire (GB)

( * ) Notice: Subject to any disclaimer, the term of this patent is extended or adjusted under 35 U.S.C. 154(b) by 239 days.

(21) Appl. No.: 10/552,543

(22) PCT Filed: Apr. 14, 2004

(86) PCT No.: PCT/GB2004/001621
§ 371 (c)(1),
(2), (4) Date: Aug. 30, 2006

(87) PCT Pub. No.: WO2004/089263
PCT Pub. Date: Oct. 21, 2004

(65) Prior Publication Data
US 2007/0010773 A1 Jan. 11, 2007

(30) Foreign Application Priority Data

Apr. 14, 2003 (GB) .................................. 0308607.1
Apr. 29, 2003 (GB) .................................. 0309826.6

(51) Int. Cl.
A61F 5/00 (2006.01)
(52) U.S. Cl. .................. 602/27; 602/5; 602/23; 602/28
(58) Field of Classification Search .................. 602/65, 602/5, 27–29, 16, 60–64; 128/882; 2/239; D24/190–191
See application file for complete search history.

(56) References Cited

U.S. PATENT DOCUMENTS

| 3,504,668 A | 4/1970 | Boudon | 128/80 |
|---|---|---|---|
| 3,589,359 A | 6/1971 | Hill | 128/80 |
| 3,976,059 A | 8/1976 | Lonardo | 128/80 |
| 4,187,844 A | 2/1980 | Caprio, Jr. | 128/166 |
| 4,559,934 A * | 12/1985 | Philipp | 602/27 |
| 4,651,723 A | 3/1987 | Satoh | 128/80 |
| 4,862,900 A | 9/1989 | Hefele | 128/80 |
| 4,974,343 A | 12/1990 | Davidson | 36/89 |
| 5,185,000 A | 2/1993 | Brandt et al. | 602/63 |
| 5,219,324 A | 6/1993 | Hall | 602/28 |
| 5,257,969 A | 11/1993 | Mance | 602/28 |
| D350,204 S * | 8/1994 | Mance | D24/192 |
| 5,378,224 A * | 1/1995 | Billotti | 602/13 |
| 5,399,155 A * | 3/1995 | Strassburg et al. | 602/28 |
| 5,445,603 A | 8/1995 | Wilkerson | 602/27 |
| 5,464,384 A | 11/1995 | Cromartie | 602/27 |
| 5,472,414 A | 12/1995 | Detty | 602/27 |
| 5,584,799 A | 12/1996 | Gray | 602/5 |
| 5,676,641 A | 10/1997 | Arensdorf et al. | 602/27 |
| 6,430,970 B1 * | 8/2002 | Gardon-Mollard et al. | 66/178 A |

(Continued)

FOREIGN PATENT DOCUMENTS

CA 2 037 546 C 7/2002

(Continued)

Primary Examiner — Kim M Lewis
(74) Attorney, Agent, or Firm — Mintz Levin Cohn Ferris Glovsky and Popeo, P.C.

(57) ABSTRACT

An ankle-foot orthosis that comprises: an elastic structure (50) formed of contiguous first (52) and second (54) tubular members, the second tubular member being set at an angle to the first tubular member to define, at least in use, a generally L-shaped cavity (56) configured to accept and fit closely about the foot and ankle of a patient; and a rib (58) which is permanently bonded or otherwise permanently affixed to a region of the structure which overlies the dorsum of the patient's foot in use, said the rib being formed of a flexible material that has a resilience appropriate for resisting the particular degree of plantarflexion experienced by the patient.

20 Claims, 5 Drawing Sheets

U.S. PATENT DOCUMENTS

| | | | |
|---|---|---|---|
| 6,592,539 B1 * | 7/2003 | Einarsson et al. | 602/62 |
| 6,908,445 B2 * | 6/2005 | Watts | 602/28 |
| 7,125,392 B2 * | 10/2006 | Scott | 602/23 |
| 7,354,413 B2 * | 4/2008 | Fisher | 602/29 |

FOREIGN PATENT DOCUMENTS

| | | |
|---|---|---|
| CN | 87206215 U | 4/1988 |
| CN | 1082866 A | 3/1994 |
| CN | 1158243 A | 9/1997 |
| CN | 1203765 A | 1/1999 |
| CN | 1308514 A | 8/2001 |
| EP | 0 114 560 A2 | 12/1983 |
| EP | 0 466 100 A1 | 7/1991 |
| EP | 0 884 036 A1 | 12/1998 |
| GB | 2 188 550 A | 10/1987 |
| GB | 2 298 140 A | 8/1996 |
| GB | 2 330 309 A | 4/1999 |
| GB | 2 375 962 A | 12/2002 |
| WO | WO 94/09727 | 10/1993 |
| WO | WO 94/00083 | 1/1994 |
| WO | WO 9918896 A1 * | 4/1999 |

* cited by examiner

ANKLE-FOOT ORTHOSIS

RELATED APPLICATIONS

The present application is a national stage application pursuant to 35 U.S.C. §371, which claims priority to the prior filed International Application Number PCT/GB2004/001621, having the international filing date of Apr. 14, 2004, which claims priority to foreign patent application number GB0308607.1, filed on Apr. 14, 2003, and to foreign patent application number GB0309826.6, filed on Apr. 29, 2003.

FIELD OF THE INVENTION

This invention relates to ankle-foot orthoses.

BACKGROUND TO THE INVENTION

Orthoses are mechanical devices which impose forces upon a limb of a patient and which can be used for a variety of different purposes. For example, orthoses can be provided for supportive, functional, corrective or protective purposes, or indeed for a combination of these.

Ankle-foot orthoses are typically used to provide protection to the ankle and foot of a patient as well as to provide support against excessive plantarflexion, or "foot-drop" as it is more colloquially known Foot plantarflexion is a medical condition that results from disease, trauma or congenital abnormality. Patients affected by the condition typically experience difficulty in walking as their feet tend to drop when lifted off the ground, and to avoid stumbling they typically have to lift their foot higher than they would otherwise have to. It is also not atypical for patients to have problems during the swing through phase of their gait cycle, as a typical sufferer will tend also to exhibit poor, or impaired, dorsiflexion.

The primary function of an ankle-foot orthosis to provide a resistance to plantarflexion which helps keep the patient's foot in the correct position when the foot is lifted off the ground. As well as this resistive function, a good ankle-foot orthosis should also provide a degree of assistance to dorsiflexion during the swing through phase of the patient's gait.

A variety of different ankle-foot orthoses have previously been proposed for resisting plantarflexion, and in some cases for additionally assisting dorsiflexion.

Figure 1:
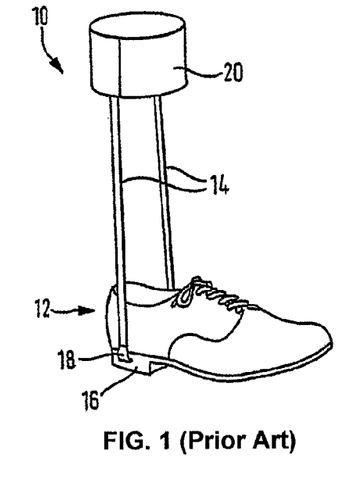
FIGS. 1 and 2 are schematic representations of a previously proposed under-foot orthosis.
Figure 2:
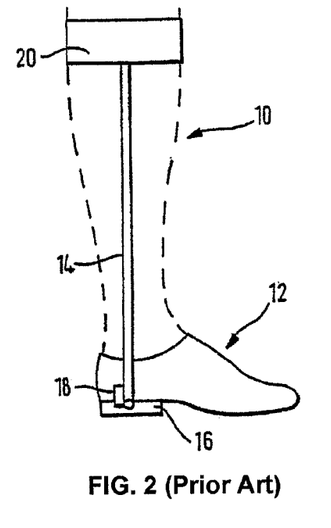

FIGS. 1 and 2 are schematic representations of what is commonly known in the art as an "under foot" orthosis 10. As this colloquial name suggests, the orthosis fits under the foot, and in this case outside of a shoe 12. This particular device cannot be worn without a shoe, and as such the shoe is an integral component of the orthosis. The orthosis comprises a pair of supporting metal rods 14, one connected to either side of the shoe 12 in the region of the heel 16. The rods are each connected to the shoe by means of a plantarflexion stop 18 that resists foot drop, and springs (not shown) may be provided to assist dorsiflexion. The upper ends of the rods are connected to a supporting band which is adapted to be secured about the calf of a patient. From FIG. 2 it can be seen that the supporting strap functions to secure the orthosis about the patient's calf, and the plantarflexion stops 18 and shoe 12 provide support under the patient's foot to resist plantarflexion.

Figures 3, 4:
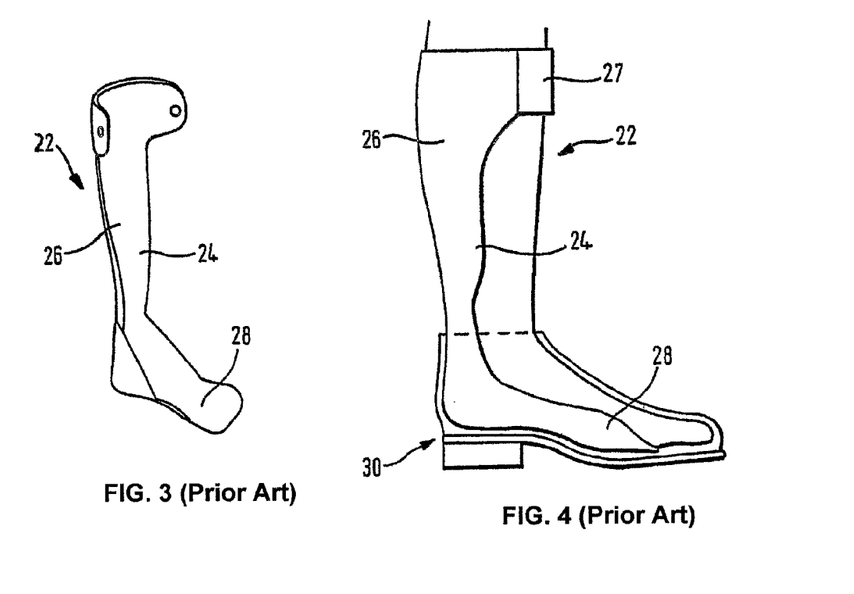
FIGS. 3 and 4 are schematic representations of another previously proposed under-foot orthosis.

FIGS. 3 and 4 illustrate another previously proposed "under foot" orthosis which must also be used with a shoe that provides close contact between the shoe and the foot in the region of the instep. In this example, the orthosis 22 comprises a one-piece plastics moulding 24 which comprises a calf-abutting region 26 and a sole abutting region 28. The top of the calf-abutting region 26 is provided with a closure mechanism 27 that enables the device to be secured to the calf of a patient. The sole abutting region 28 acts in conjunction with the shoe 30 to support the foot of the patient. The stiffness of the plastics moulding and the shape thereof in the region of the ankle defines the amount of resistance to plantarflexion. If more resistance is required, then the gap across the front of the ankle can be reduced, or the stiffiess of the plastics material can be increased.

Figure 5:
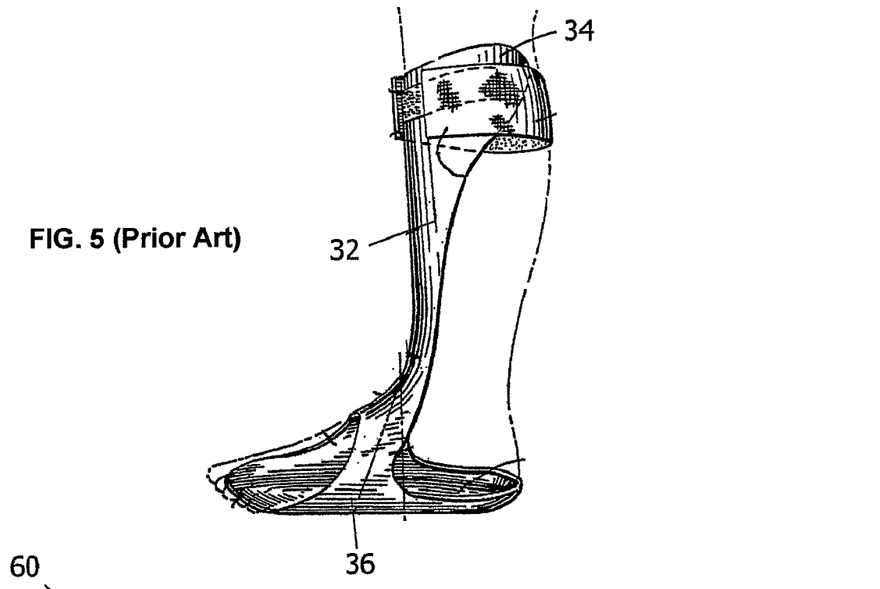
FIG. 5 is a schematic representation of a previously proposed over-foot orthosis.

FIG. 5 is a functional equivalent to the orthosis of FIGS. 3 and 4, and as such is similar in many respects to the orthosis shown in FIGS. 3 and 4. The chief difference is that the device shown in FIG. 5 is an "over foot" orthosis, meaning that the orthosis fits over the front (dorsal) aspect of the foot, rather than under it as in the device of FIGS. 1 to 4. As shown the device comprises a plastics shell 32 which is worn up against the shin, and which is secured around the calf by means of an appropriate securing band 34. The orthosis includes a stirrup 36 which fits over the foot in the region of the instep, and it is the stirrup which provides the patient with a resistance to plantarflexion.

All of the aforementioned orthoses are sufficient to provide a patient with a device which is operable to resist plantarflexion. However, it is also the case that each of them has a number of attendant disadvantages.

A first disadvantage is that all of the aforementioned devices are extremely large and bulky bits of equipment which are clearly visible when worn. This means that a patient wearing one of these devices is immediately singled out as being "abnormal", and this can have a particularly adverse effect on a patient's state of mind.

A further disadvantage is that all of these devices must be worn with shoes, and those shoes may have to have been specially manufactured either to include the appropriate plantarflexion stops (and optional springs), or simply to be large enough in the right places to accommodate an in-shoe medical device. As it is difficult (if not impossible) for a patient to use these devices with normal "off-the-shelf" footwear, the overall cost of the orthosis (including ongoing costs) is typically greatly increased. It also means that a patient who wishes to undertake some activity without shoes, such as swimming for example, would have to undertake that activity without having been provided with any means for resisting plantarflexion.

Another financial disadvantage of these devices is associated with the fact that they each need to be tailored for a particular patient, and fitted by a competent professional. For example, the devices shown in FIGS. 3 to 5 all must be closely moulded by a technician to the shape of the patient's foot and leg, and the fitting process will most likely have to be repeated each time the patient acquires a new pair of shoes.

Another disadvantage associated particularly with the orthoses shown in FIGS. 3 to 5 is that they can be very uncomfortable to wear as the weight of the patient is always bearing down onto a rigid plastics shell. It is not uncommon for the shell to dig into the sole of the patient's foot and cause quite considerable discomfort.

Yet another attendant disadvantage associated particularly with the orthoses shown in FIGS. 3 to 5 is that they typically provide very little dynamic assistance to dorsiflexion of the patient's foot. Typically, the plastics materials used are such that they are relatively difficult to flex and bend, and this means that they are not good at storing energy which can be released to assist dorsiflexion during the swing through phase of a patient's gait cycle.
}

Another previously proposed orthosis, which avoids some of the aforementioned problems, is described in U.S. Pat. No. 4,559,934. This orthosis is composed of four discrete components, namely an elastic support stocking, a dorsal plate which is anatomically fitted to the dorsum of the foot, an elastic connector which is connected to the bottom end of the plate, and a retaining fitting to which the elastic connector is attached in use. The elastic stocking comprises a standard elastic support stocking such as may be purchased in any pharmacy or chemist, and the plate is attached to the stocking by means of a pair of pockets which are sewn onto the sock. Once the plate has been fitted into the pockets, the elastic connector is drawn through a slit in the plate, and adhered—for example by means of a mechanical hook and loop fastener—to the retaining fitting. By selecting an appropriate tension for the elastic, the foot of the patient can be raised to the required degree.

This device is significantly more inconspicuous and comfortable than the devices shown in FIGS. 1 to 5. However, it still is reasonably noticeable, particularly when the foot is viewed side-on.

It is also the case that it is typically quite difficult for a patient to put the device on and take the device off (due to the number of separate components), and it is very easy for the patient to inadvertently select an insufficient or excessive resistance to plantarflexion simply by pulling too little or too much of the elastic through the slit. This last disadvantage is exacerbated by the fact that it is difficult for the patient to adjust the resistance to plantarflexion when their foot is off the ground, and as a consequence it is not uncommon for a patient wearing such a device to take several attempts to adjust it correctly.

To alleviate the problems set out above, we have previously provided (see granted UK Patent No. 2330309) a sock-like structure which is formed of a resiliently flexible material—such as silicone for example. The sock-like structure, by virtue of its resilience, provides a resistance to plantarflexion and the inherent resilience of the material allows it to store energy which can be released to assist dorsiflexion. The orthosis can be coloured to mimic the colour of the patient's skin (and as such it is cosmetically pleasing), can comfortably be worn in a normal off-the-shelf shoe, and need not be worn with a shoe in order to provide a beneficial effect.

This orthosis provides a quantum leap in the field, and alleviates most of the disadvantages set out above. However, it does still suffer from the disadvantage that it must be carefully fitted by a clinical technician. This means that it can take a considerable amount of time to make and fit the orthosis, and the most immediate drawback of this is that our previously proposed device is still relatively expensive.

It is an aim of the present invention to provide an orthosis which avoids, or at least alleviates, the problems set out above. In particular, it is an aim of the invention to provide an orthosis which functions comparably well to that which we previously proposed, whilst being significantly less expensive to produce.

STATEMENT OF INVENTION

In pursuit of the above mentioned aims, a preferred embodiment of the invention provides an ankle-foot orthosis that comprises: an elastic (sock-like) structure formed of contiguous first and second tubular members, said second tubular member being set at an angle to the first tubular member to define, at least in use, a generally L-shaped cavity configured to accept and fit closely about the foot and ankle of a patient; and a rib which is permanently bonded or otherwise permanently affixed to a region of the structure which overlies the dorsum of the patient's foot in use, said rib being formed of a flexible material that has a resilience appropriate for resisting the particular degree of plantarflexion experienced by the patient.

The principal advantage of this orthosis, over that which we previously proposed, is that is it significantly less expensive to manufacture. For this reason, our new orthosis is well suited for commercial retail purposes, for example in chemists or pharmacies, where patients can purchase suitable devices with the minimum of professional assistance. Further advantages of our orthosis (as compared to other previously proposed devices) are: (a) it can be put on and taken off quickly, (b) it is highly inconspicuous, (c) it does not need adjusting, (d) it does not need to be worn with a shoe, and (e) it is significantly more comfortable than some previously proposed devices.

In a highly preferred embodiment, the elastic structure comprises a compression stocking operable to exert a compressive force of more or less than at least 5 mm Hg (approximately 670 Pascals) on the foot and ankle of the patient.

In another highly preferred embodiment, the rib is of silicone elastomer. The resilience of the rib may be varied by, for example, varying the thickness of the rib. Alternatively, or additionally, the resilience of the rib may be varied by varying the composition of the elastomer. The rib could be, for example, of 35 to 80 shore silicone elastomer, preferably 65 shore silicone elastomer.

Further objects, features and advantages of embodiments of the invention will be apparent from the description which follows:

BRIEF DESCRIPTION OF THE DRAWINGS

Various preferred embodiments of the invention will now be described, by way of illustrative example only, with reference to the accompanying drawings, in which.

DETAILED DESCRIPTION OF PREFERRED EMBODIMENT

Figure 6A:
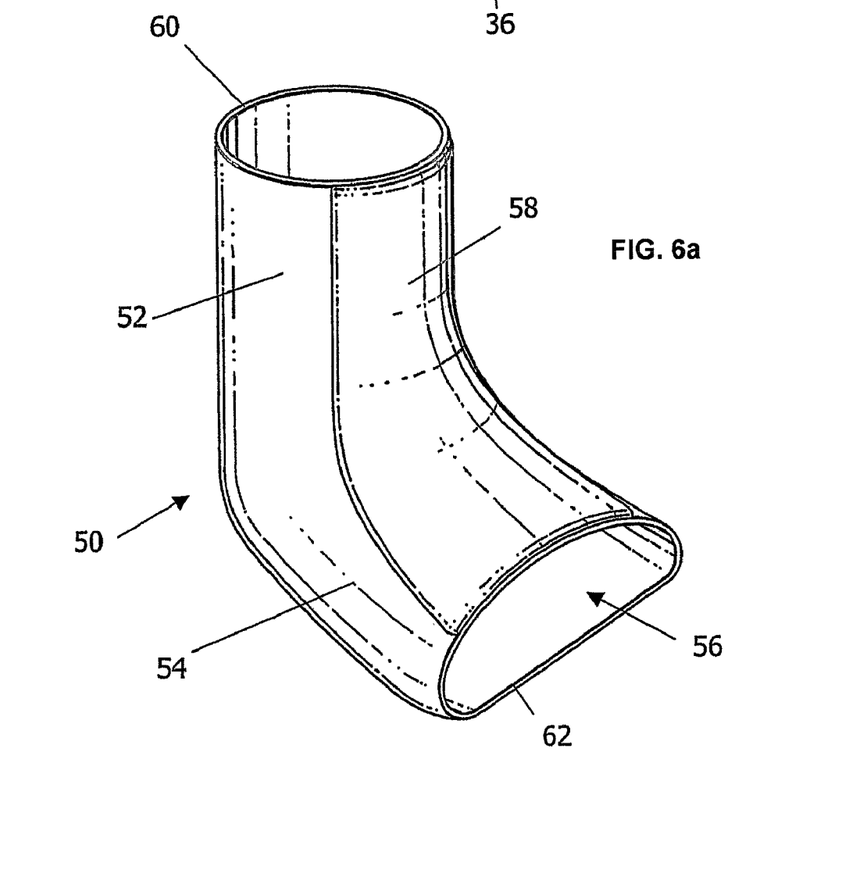
FIGS. 6a and 6b are schematic representations of an orthosis in accordance with an embodiment of the invention.

FIG. 6a is a perspective view of an embodiment of the invention. The orthosis depicted in FIG. 6a is shown as it would appear when worn by a patient (the patient's foot and ankle having been omitted for clarity). When not being worn by the patient, the orthosis assumes a more two-dimensional shape to facilitate storage.

As shown, the orthosis comprises an elastic generally sock-like structure 50. The sock is comprised of a first tubular portion 52, and a contiguous second tubular portion 54 which in most instances will have been integrally formed with the first tubular portion.

The first and second tubular portions are set at an angle to one another to provide, at least in use, a generally L-shaped internal cavity 56 which is sized to accept and fit closely about the foot and ankle of a patient (not shown).

A resiliently flexible rib 58 is provided on the structure, and extends from a proximal edge 60 of the orthosis (which locates on or slightly above the ankle of the patient when worn) to a distal edge 62 of the orthosis (which locates in the region of the metatarsal heads when worn by the patient) along the dorsum of the patient's foot. The rib is formed to have a curved cross-sectional shape (i.e. to be concave when viewed from the cavity 56), and the rib's radius of curvature is chosen to be less than the radius of curvature of a typical foot.

When the orthosis is worn by a patient, the patient's foot and lower leg bias the rib (against its natural resilience) to increase its radius of curvature so that it matches that of the patient's foot and lower leg. Increasing the rib's radius of curvature causes the rib, by virtue of its inherent resilience, to exert a compressive force on the dorsum of the patient's foot and this force allows the rib to firmly grip the patient's foot.

As mentioned above, the rib of this embodiment is permanently attached to the structure during the orthosis' manufacture. The resilience of the rib can be tailored to provide a resilience that is appropriate for resisting the particular degree of plantarflexion experienced by the patient.

In an alternative arrangement that is particularly well suited for mass-production, manufactured orthoses may be provided with a resilience that falls within one of a number of discrete ranges—for example a low resilience, a medium resilience and a high resilience. Any given patient then need only select an orthosis with a resilience that is appropriate for the particular degree of plantarflexion that they experience.

In a highly preferred embodiment, the rib 58 is formed of silicone elastomer directly onto the structure 50. It is conceivable that other materials could be used, such as rubber, polypropylene or plastics—but the highly resilient nature of silicone coupled with its ease of use means that it is necessarily the most preferred material. In the preferred arrangement, the rib 58 is formed on the structure such that the silicone is impregnated into the material of the structure to form a permanent bond between the silicone rib and the structure along the entire length of the rib.

The use of a resilient material is a fundamental departure from prior teachings which tended to recommend the use of a non-resilient, i.e. rigid, material. The primary advantage of using a resilient material as opposed to a rigid material is that the material can flex to store energy during certain phases of the patient's gait, and release that energy during other phases of the patient's gait to thereby actively assist the walking process.

The rib may be formed on the structure in any of a number of different ways that will be apparent to persons skilled in the art. By way of illustrative example a so-called milling process more suited for the manual production of a silicone rib will now be described. Methods more appropriate for mass-production are currently being developed. As an alternative to forming the rib on the structure, it could of course be formed separately and then permanently affixed to the structure by means of an adhesive or any other suitable mechanism.

In this illustrative example, the silicone could be one of two suitable elastomers, HCR9960 and MED4035, both of which are sold by Nusil Technology of 1050 Cindy Lane, Carpinteria, Calif., USA. HCR9960 has a working time of approximately 12 hours, whereas MED4035 has a shorter working time of roughly 3 to 4 hours, after which the elastomer cures. The elastomers are thermosetting, and are preferably strained through a 200 mesh screen to remove particulate contaminants before the rib is formed.

Both of these elastomers are supplied as A and B components, which are then subsequently combined on a rolling mill, or other suitable device, prior to use. In this example, equal measures of A and B components are used and the B component is first softened on the rolling mill following which the A component is then softened on the mill. An equal weight of component B is then added to component A, and the two components are then thoroughly mixed. At this stage it is recommended to keep the temperature of the material as low as possible so as to maximise the table life of the elastomer.

Once thoroughly mixed, the elastomer may then be built up in layers on a sock-like structure 50 which has been stretched over an approximately foot-shaped anvil. The elastomer is then left for 3 to 4 hours to cure—although this may be accelerated by heat. Once the elastomer has cured the structure 50 can be removed from the anvil, whereupon the natural resilience of the elastomer causes the rib to curl inwards to increase it's radius of curvature—the resulting advantage of this having previously been described herein.

The resilience of the rib may be varied as required to provide a appropriate for alleviating the particular severity of the condition experienced by the patient. This variance in resilience may be provided, for example, by varying the thickness of the rib. Alternatively, or additionally, the resilience of the rib may be varied by varying the composition of the elastomer. As an illustrative example, the rib could be of 35 to 80 shore silicone elastomer, preferably 65 shore silicone elastomer.

The sock-like structure 50 of this embodiment is, as has been mentioned above, of an elastic material, and in a highly preferred embodiment is sufficiently elastic to exert a compressive force on the foot and ankle of the patient. That force may be more or less than at least 5 mm Hg (roughly 670 Pascals).

The sock-like structure may be of a woven elastic one-way stretch construction. By this we mean that the elastic structure may be woven from individual elastic fibres such that it may only stretch in an outward direction to increase the cross-sectional area of the L-shaped cavity, and not in a direction which would increase the length of the orthosis. The elastic structure could alternatively be designed so that it exhibits a greater potential for stretching in a direction which would increase the cross-sectional area of the L-shaped cavity, than in a direction which would increase the length of the orthosis.

In general terms the sock-like structure may be a so-called compression stocking, and a distinction should be drawn between this type of elastic stocking and a commonly available support stocking of the type that may be purchased in any chemist or pharmacy. Support stockings sold under the trade name Tubigrip® are one example of a commonly available support stocking, and this Tubigrip® stocking exerts much less of a compressive force on the foot and ankle of the wearer than a compression stocking of the type referred to herein.

Whilst it would of course be possible to form a silicone rib on one of these typical Tubigrip® support stockings, the stocking would provide insufficient elastic force to keep the rib in close abutment with the lower leg of the patient whilst walking. In particular, it is likely that the weight of a foot (and shoe) lifted off the ground would simply cause the proximal end of the stocking to elastically overextend with the result that the rib would then no longer be in abutment with the lower leg, and the foot would be allowed to drop.

In contrast, compression stockings of the ilk referred to herein exhibit an elastic force which is sufficient to keep the rib in close abutment with the lower leg of the patient when the patient's foot is off the ground. This is important because at this point in the patient's gait it is, of course, only the close coupling of the rib to the leg provided by the elastic stocking which keeps the patient's foot in the correct position.

In general terms, support stockings (of which Tubigrip® stockings are an illustrative example) are provided to control lateral movement of the ankle of a patient in an effort to avoid or alleviate ankle sprains, such sprains typically involving damage to the lower extensor muscle retinaculum (a muscle which supports lateral movement of the ankle).

The device of the present invention, in stark contrast, provides a means for resisting plantarflexion and assisting dorsiflexion of the patient's foot during, for example, the swing-through phase of the gait cycle. Dorsiflexion and plantarflexion of a foot is predominantly controlled by the tibialis anterior muscle and tendon, and the structure of the invention functions to assist the operation of this muscle—in particular for those patients who experience persisting foot drop resulting from a neurological impairment caused, for example, by trauma, disease or genetics. This bio-mechanical function of the device of the invention is fundamentally different to support stockings of the type aforementioned which provide no means for assisting the operation of the tibialis anterior muscle and tendon (to resist plantarflexion and assist dorsiflexion of a patient's foot), and are instead wholly concerned with resisting abnormal lateral movement of the foot.

As with the resilience of the rib, the compressive force provided by the sock-like structure may be varied to, for example, help treat other conditions such as the effects and symptoms of venous insufficiency, for example varicose veins. It is also conceivable for different regions of the sock-like structure to provide different compressive forces. For example, the sock-like structure may exert a greater compressive force on the foot of the patient than on the ankle in order to provide a pumping effect to assist blood flow to and from the foot.

To make it even easier for the patient to put on and take off the orthosis, the sock-like structure of any embodiment disclosed herein may be formed with an insertion slit (not shown) running down the back of the patient's lower leg toward the ankle. The insertion slit can be closed, once the patient has put on the device, by any of a number of different mechanisms. For example, one side of the slit could be formed with a tab, the underside of which is provided with one part of a two-part mechanical hook-and-loop fastener (such as Velcro®, for example), the other part of the fastener being secured to the sock-like structure. As an alternative, either side of the slit could be provided with a series of eyes which can be closed by means of a lace threaded therethrough.

Figure 6B:
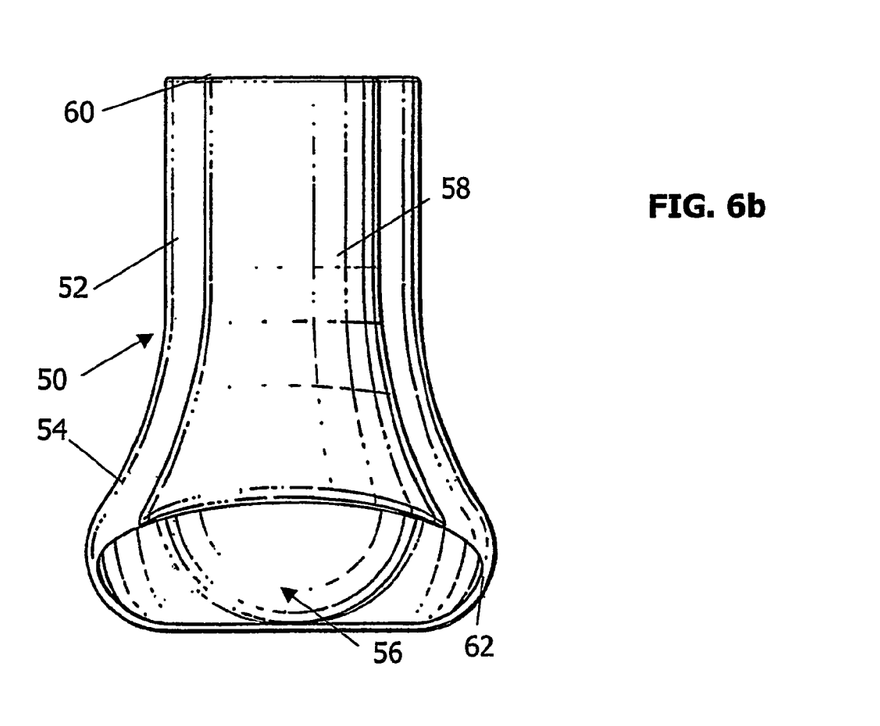

FIG. 6b is a front view of the orthosis shown in FIG. 6a illustrating the manner in which the rib 58 extends from the proximal edge 60 of the sock-like structure 50 of the orthosis down the dorsum of the foot to the distal edge 62 of the structure 50.

Figure 7A:
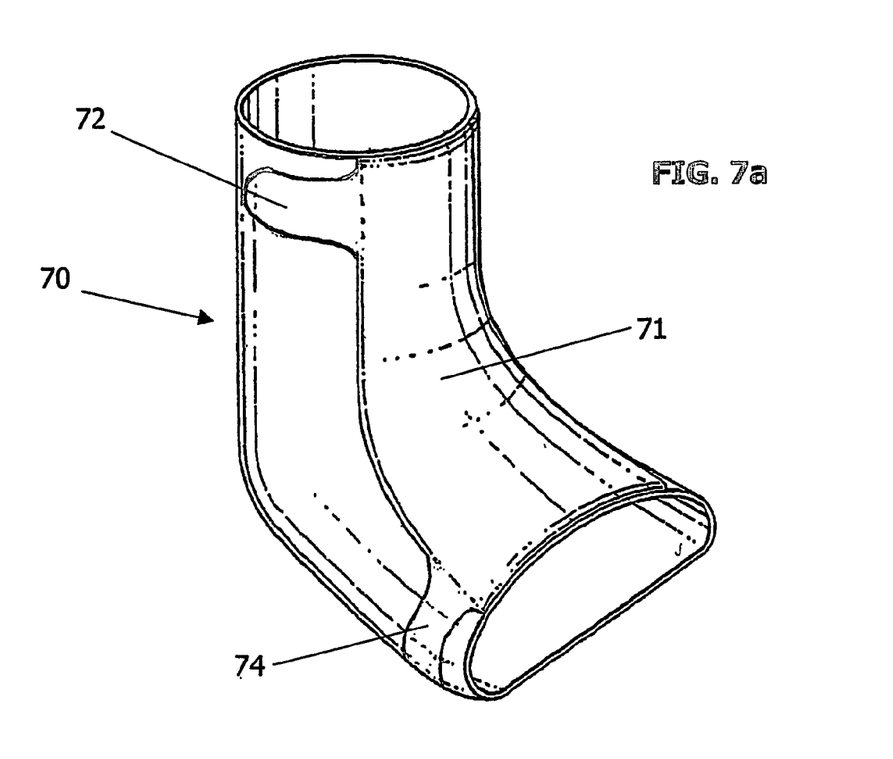
FIGS. 7a to 7e are schematic representations of an orthosis in accordance with another embodiment of the invention.

FIG. 7a is a perspective view of another embodiment of the invention. The orthosis of this embodiment is similar in a number of respects to that of the previous embodiment in that it comprises a generally sock-like structure 70 on which a rib 71 has been formed or otherwise provided. For brevity, features common between the two embodiments will not further be described.

The principal difference between the orthoses of the two embodiments, is that in this embodiment the rib 71 is provided with proximal 72 and distal 74 pairs of wings that extend from the rib towards the back of the ankle and the plantar aspect of the foot, respectively.

The wings 72, 74 function to increase the lateral stability of the orthosis, and as such the orthosis of this embodiment is particularly well suited for those patients who have weak ankles, as well as problems with resisting plantarflexion. The proximal wings 72 help reduce the chance of the patient rolling over on their ankle by providing a lateral and medial stabilising force to the patient's ankle. The distal wings 74 assist with this function, as well as helping to keep the rib properly aligned with the dorsum of the patient.

The resilience of the wing(s) and rib may be the same or similar, or alternatively, the resilience may be different to account for patients who exhibit—for example—a greater disposition towards rolling over onto their ankle than plantarflexion. It should also be noted that the wings need not be of the same material as the rib.

Figure 7B:
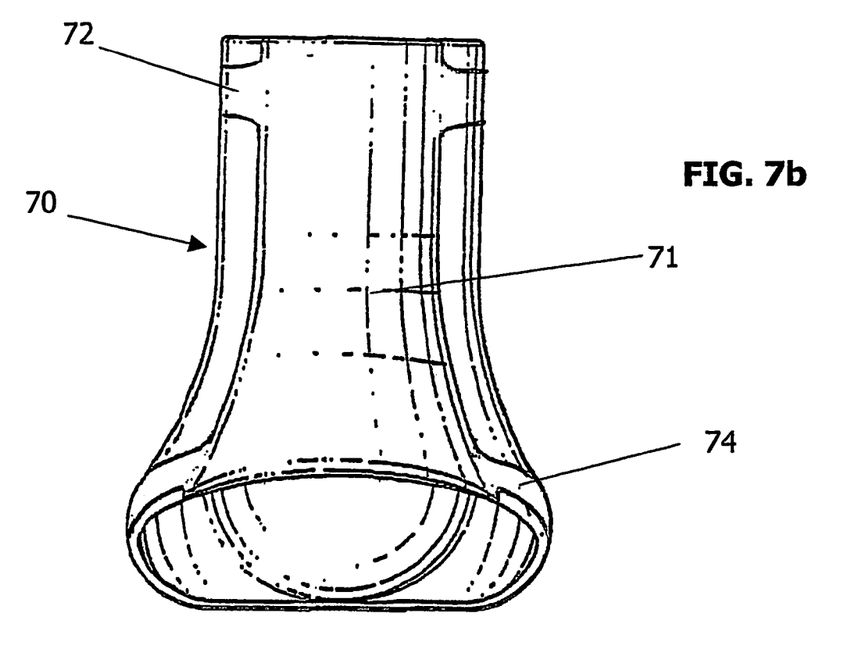
Figure 7C:
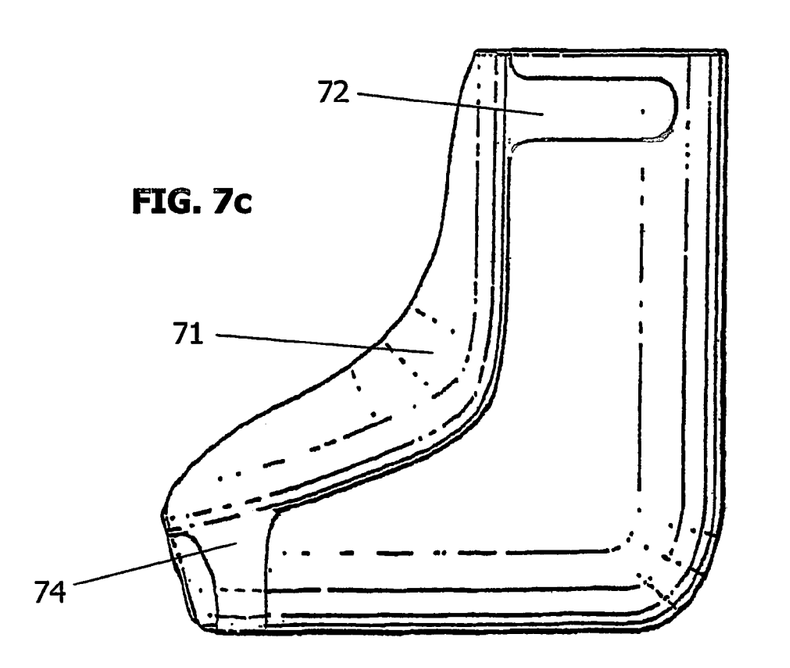
Figure 7D:
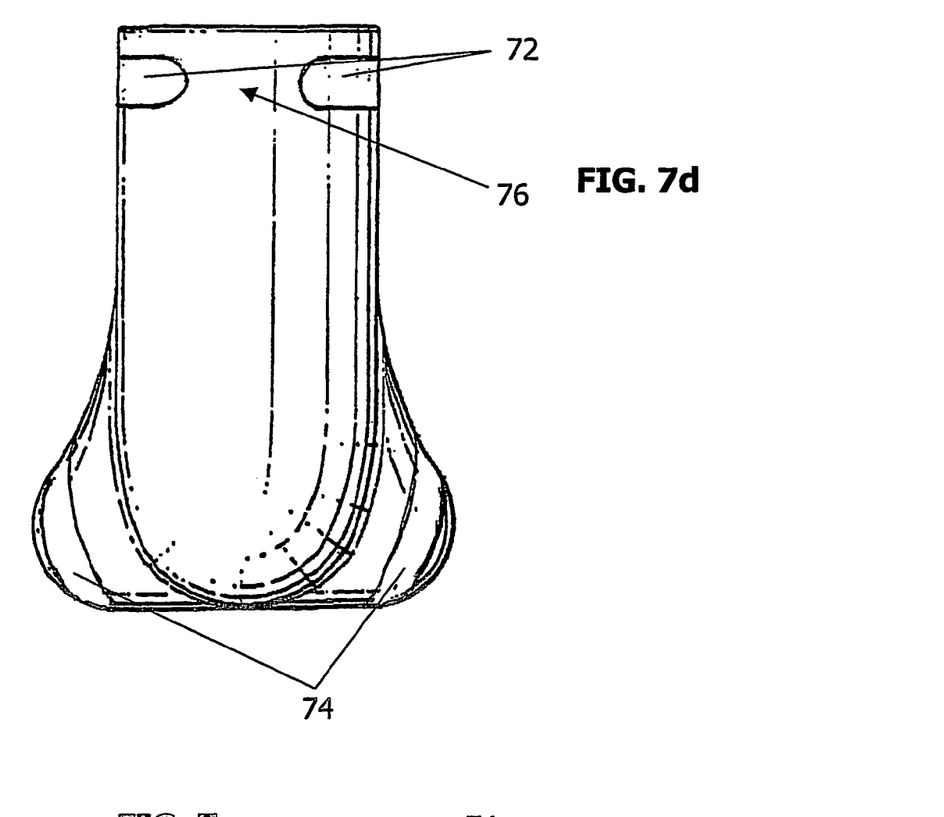
Figure 7E:
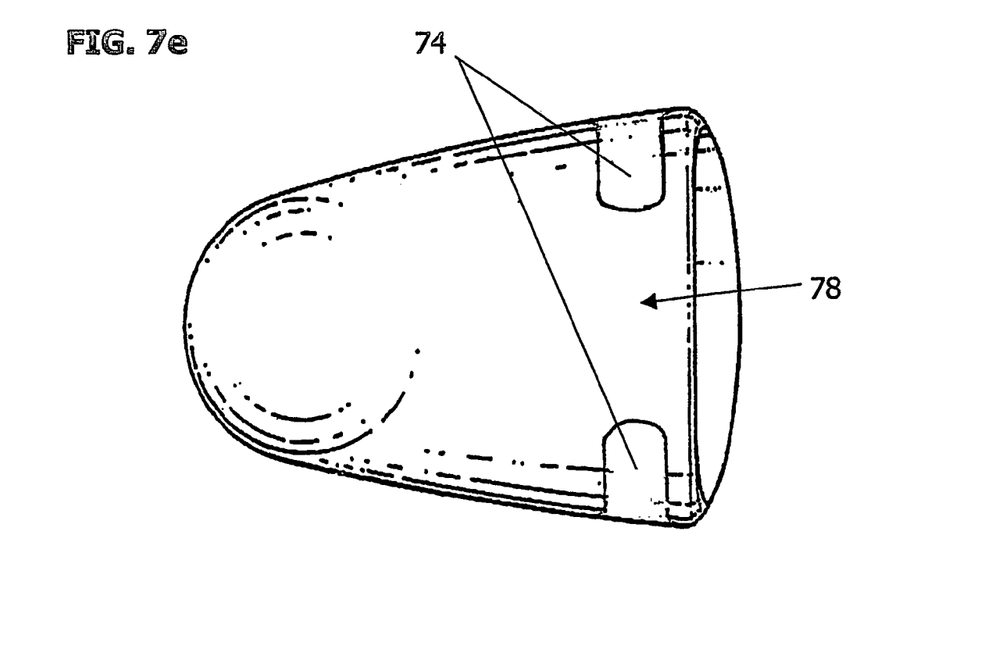

FIGS. 7b and 7c are, respectively, front and side views of the sock illustrating how the rib extends around the ankle and foot to form the aforementioned wings. FIGS. 7d and 7e are, respectively rear and underneath plan views of the orthosis.

FIG. 7d shows how the proximal wings 72 extend around either side of the ankle. As shown, a gap 76 is left so that the sock-like structure is still sufficiently elastic in the region of the proximal edge of the orthosis to allow a patient to put on the orthosis.

FIG. 7e shows how the distal wings 74 extend around and partly underneath the foot, again leaving a gap 78 so that the orthosis is sufficiently elastic in the region of the distal edge to allow a patient to put it on.

It will be understood from the above that the orthoses of the preferred embodiments provide an effective means to tackle the problem of plantarflexion. Advantageously, and in addition to this function, the orthoses of the invention can significantly augment dorsiflexion during the swing through phase of a patient's gait cycle. The principal reason for this is believed to be that the elastic structure and resilient rib store energy when compressed, and this energy is released during the swing through phase of the patient's gait cycle. It is anticipated, therefore, that patients will not only find that the orthoses of the embodiments tackle the problem of plantarflexion but also actively assist the walking process.

Our previously proposed device (as described in granted UK Patent No. 2330309) was found to provide a considerable improvement not only to the degree of plantarflexion, but also to the walking speed and the effort involved in walking (known as the Physiological Cost Index or PCI) of a group of patients. At an initial point in the study it was found that the orthosis provided an increase of roughly 10% in walking speed and a reduction of roughly 2% in the PCI. At the end of the study, roughly six months later, it was found that that same group of patients experienced an increase in walking speed of roughly 20% and a reduction of roughly 32% in the PCI as compared to when they were initially without the orthosis. It is anticipated that the orthosis of the present invention will provide similar, and hopefully, better results.

Whilst various preferred embodiments have been described above in detail, it will be apparent and should be noted that modifications and alterations may be made without departing from the spirit and scope of the invention as defined by the accompanying claims.

For example, the embodiment depicted in FIGS. 7a to 7e may be modified to include only a single pair of wings (distal or proximal) or indeed to include further pairs of wings extending from the rib in between the aforementioned proximal and distal pairs of wings.

The invention claimed is:
1. An ankle-foot orthosis for resisting plantarflexion of a patient's foot, the orthosis comprising:
 a compression stocking formed of contiguous first and second tubular members, said second tubular member being set at an angle to the first tubular member to define, at least in use, a generally L-shaped cavity configured to accept and fit closely about the foot and ankle of the patient; and a flexible rib of silicone elastomer, at least a portion of an external surface of a defined region of the compression stocking; said defined region being substantially aligned with at least a portion of the dorsum of the patient's foot when said orthosis is in use; being impregnated with said silicone rib to bond said rib to said defined region of the compression stocking, such that said rib overlies at least a portion of the dorsum of the patient's foot when said orthosis is in use and has a resilience that is appropriate for resisting the particular degree of plantarflexion experienced by the patient.

2. An orthosis according to claim 1, wherein said compression stocking is operable to exert a compressive force on said foot and ankle of said patient.

3. An orthosis according to claim 2, wherein said compressive force is more or less than at least 5 mm Hg (approximately 670 Pascals).

4. An orthosis according to claim 2, wherein different regions of the compression stocking exert different compressive forces on the foot and ankle of the patient.

5. An orthosis according to claim 4, wherein said second tubular member exerts a greater compressive force on the foot than the compressive force exerted on the ankle by the first tubular member.

6. An orthosis according to claim 1, wherein said compression stocking is woven to provide an elastic stretch in only one direction, said one direction comprising a direction that increases the cross-sectional area of said generally L-shaped cavity.

7. An orthosis according to claim 1, wherein the resilience of the rib, as between a first orthosis and a second orthosis, may be varied by varying the thickness of the rib of one orthosis as compared to the other.

8. An orthosis according to claim 1, wherein the resilience of the rib, as between a first orthosis and a second orthosis, may be varied by varying the composition of the rib of one orthosis as compared to the other.

9. An orthosis according to claim 1, wherein the rib is of 35 to 80 shore silicone elastomer.

10. An ankle foot orthosis according to claim 9, wherein said rib is of 65 shore silicone elastomer.

11. An orthosis according to claim 1, wherein said rib comprises a pair of proximal wings extending from the rib around either side of the ankle of the patient towards the back of the ankle, said wings terminating at the back of the ankle and defining a gap between a terminal end of each wing.

12. An orthosis according to claim 11, wherein said proximal wings extend in parallel to a proximal edge of the elastic structure.

13. An orthosis according to claim 11, wherein said proximal wings have the same resilience or a different resilience to that of the rib.

14. An orthosis according to claim 1, wherein said rib comprises a pair of distal wings extending from the rib around and partly underneath the foot, in the region of the metatarsal heads, towards the plantar aspect of the foot, said wings terminating underneath the foot and defining a gap between a terminal end of each wing.

15. An orthosis according to claim 14, wherein said distal wings extend generally in parallel to a distal edge of the compression stocking.

16. An orthosis according to claim 14, wherein said distal wings have the same resilience or a different resilience to that of the rib.

17. An orthosis according to claim 1, wherein said rib comprises a pair of proximal wings extending from the rib towards the back of the ankle of the patient, and further comprises a pair of distal wings extending from the rib, in the region of the metatarsal heads, towards the plantar aspect of the foot.

18. The orthosis according to claim 1, wherein said rib includes one or more layers of silicone elastomer.

19. A method of manufacturing an orthosis for resisting plantarflexion of patient's foot, the method comprising the steps of:

providing a compression stocking formed of contiguous first and second tubular members set at an angle to one another to define, at least in use, a generally L-shaped cavity configured to accept and fit closely about the foot and ankle of a patient;

mounting the compression stocking on a foot-shaped anvil;

preparing a silicone elastomer having a resilience which is appropriate for resisting the particular degree of plantarflexion experienced by the patient;

applying the silicone elastomer directly to at least a portion of an external surface of a defined region of the compression stocking; said defined region being substantially aligned with at least a portion of the dorsum of the patient's foot when the orthosis is in use; such that, the silicone elastomer impregnates and bonds to the defined region of the compression stocking and forms a rib that will, in use, overlie the dorsum of the patient's foot;

curing the silicone elastomer to form a bond between the rib and the compression stocking; and removing the compression stocking from the anvil.

20. The method of claim 19, wherein applying the silicone elastomer includes applying one or more layers of silicone elastomer.

* * * * *